US007322964B2

(12) United States Patent
Pajunk et al.

(10) Patent No.: US 7,322,964 B2

(45) Date of Patent: Jan. 29, 2008

(54) CHECK VALVE FOR A TROCAR SYSTEM

(75) Inventors: Heinrich Pajunk, Geisingen (DE); Horst Pajunk, Geisingen (DE)

(73) Assignee: Gebrueder Pajunk Besitzverwaltung OHG, Geisingen (DE)

( * ) Notice: Subject to any disclaimer, the term of this patent is extended or adjusted under 35 U.S.C. 154(b) by 0 days.

(21) Appl. No.: 10/858,308

(22) Filed: Jun. 1, 2004

(65) Prior Publication Data

US 2004/0243059 A1 Dec. 2, 2004

(30) Foreign Application Priority Data

May 30, 2003 (DE) ................................ 103 24 684

(51) Int. Cl.
*A61M 5/00* (2006.01)

(52) U.S. Cl. ...................................................... 604/246

(58) Field of Classification Search ................ 604/167, 604/169, 256, 905, 283, 246, 247
See application file for complete search history.

(56) References Cited

U.S. PATENT DOCUMENTS 2,989,283 A * 6/1961 Klingler ...................... 251/86
4,654,030 A 3/1987 Moll et al.
5,397,314 A * 3/1995 Farley et al. ............... 604/256
5,460,615 A * 10/1995 Storz ..................... 604/167.03
5,820,606 A * 10/1998 Davis et al. ................ 604/256
6,077,249 A * 6/2000 Dittrich et al. ........ 604/167.03
6,228,061 B1 5/2001 Flatland et al.
6,783,516 B2 * 8/2004 O'Heeron et al. .......... 604/256

FOREIGN PATENT DOCUMENTS

DE 39 23 243 A1 1/1991
DE 197 12 726 C1 6/1998
EP 0 323 018 B1 6/1993
JP 197 54 166 A1 3/2001

* cited by examiner

*Primary Examiner*—Manuel Mendez
(74) *Attorney, Agent, or Firm*—Stephan A. Pendorf; Peter A. Chiabotti; Akerman Senterfitt

(57) ABSTRACT

A flap valve for a trocar system including a valve housing (12) that is proximally attachable to a guide tube (10), a lead-through opening (30) formed in the valve housing (12), and a pivotally mounted flap valve (46). The flap valve (46) is manually pivotable from a "closed" position to an "open" position via a slide rod. The slide rod (52) is mebedded in the body (12), is radially slidable and contacts with its inner end an actuation area of the flap valve (46).

8 Claims, 4 Drawing Sheets

38
44
36
42
54
56
47
40
38
36
24
16
48
50
46

60
47
46

60
47
46
48

CHECK VALVE FOR A TROCAR SYSTEM

BACKGROUND OF THE INVENTION

1. Field of the Invention

The invention concerns a flap valve for a trocar system according to the preamble of a patent 1.

2. Description of the Related Art

Trocar systems are being used in minimally invasive surgery to enable entrance to a body cavity, for example, into the visceral cavity. For this procedure, a guide tube (trocar cannula) with a trocar (obturator) inserted therein is passed through the abdominal wall. Subsequently, the trocar is removed and the guide tube remains as an access canal to the visceral cavity. In order to perform surgical procedures in the visceral cavity, it typically is insufflated. To avoid gas leakage from the visceral cavity, a valve is placed at the extracorporeal remaining proximal end of the guide tube, which closes automatically if no instrument is inserted.

To enable the insertion of a delicate instrument and avoid the entanglement of instruments during extraction, flap valves are used that can be manually opened. The flaps on the flap valves include part of a valve that closes, spring-biased, on an aperture, which aligns axially with the guide tube. The flap is pivotally operated against a spring force, perpendicularly to the exocentric pivoting axis of the lead-through opening.

From U.S. Pat. No. 4,654,030 it is known to affix a valve non-rotatingly (torque-proof) upon a pivot axle, and to provide a pivot lever on the end of the axle projecting out from the valve body for the manual actuation of the valve. The manipulation of the flap valve is unfavorable, because the surgeon has to support the trocar system with one hand and use the other hand for pivoting the valve.

In DE 3923243 C2, a flap valve of the previously mentioned type is disclosed. This flap valve is pivoted into the open position with the aid of a sliding rod. The sliding rod is slidable parallel to the axis of the releasable lead-through-opening. To operate the flap, the housing-inner end of the sliding rod engages the flap between the valve part and its pivoting axis. The space needed to operate the slide rod enlarges the radial and axial measurements of the body of the flap valve. Because of spatial reasons the slide rod must be attached very close to the middle axis of the body, so the handling of the slide rod is ergonomically unfavorable.

The object of the invention is to provide a flap valve for a trocar system with a compact configuration that allows an ergonomically favorable handling of the tool.

This task is inventively accomplished by a flap valve having the characteristics of Patent 1.

Preferred embodiments of the invention are set forth in the dependent claims.

SUMMARY OF THE INVENTION

In the inventive flap valve, the slide rod operating the flap is introduced radially slidable into the housing. The flap valve can thus be opened simply by pushing a radially positioned push button. Therefore, it becomes possible to handle the trocar system and operate the flap valve with one hand in an ergonomically favorable manner. The housing of the flap valve and consequently the trocar system can be held, for example, between the index and middle fingers, whereas the radial operation of the flap valve can be by the thumb. The flap is constructed in the manner of a two-armed lever. The slide rod engages an actuation area that is located on one arm of the flap. The other arm, relative to the pivoting axis of the flap, includes the valve part. Preferably, the operating area is developed immediately in the area of the pivoting axis. Therefore, the operating of the flap doesn't require any additional radial space and the outside diameter of the body can stay at a minimum. In addition, a pivoting of the flap by 90° between the "closed" and "open" positions is possible through a smaller radial stroke—another advantage of the compact design of the flap valve. Especially, the radial slide rod allows a significant reduction of the axial dimensions of the flap valve.

In a preferred embodiment, the actuation area of the flap is in the form of a curved surface having such a shape that the area that slide rod engages has, in any pivoted position of the flap, as sufficiently large angle to the slide rod axis to initiate a turning moment in the pivoting direction of the flap. Through the pivoting movement of the flap, the actuation area practically slides underneath the inward facing end of the slide rod. Thus, there is a constant application of force and a constant torque over the total linear range of the slide rod and therefore the total pivoting range of the flap. This is of substantial advantage for an ergonomic operation of the flap valve.

BRIEF DESCRIPTION OF THE DRAWING

The invention will be explained in detail in the following on the basis of the embodiments shown in the figures, wherein there is shown.

DETAILED DESCRIPTION OF THE INVENTION

Figure 1:
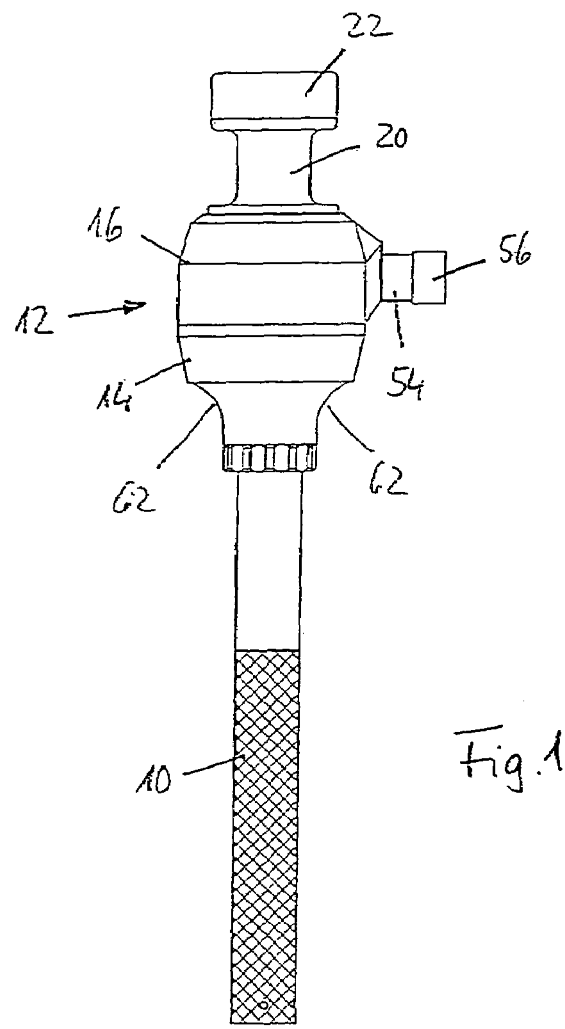
FIG. 1: a side view of the trocar system.
Figure 2:
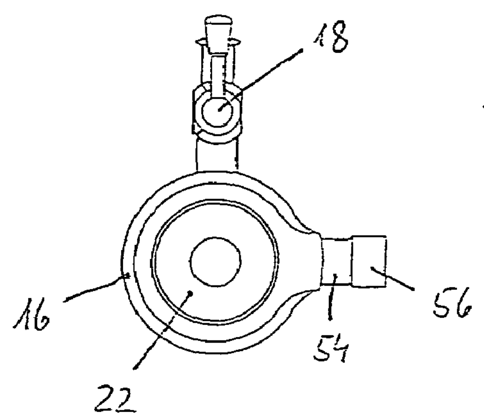
FIG. 2: an axial view of the trocar system viewed from the proximal end.
Figure 3:
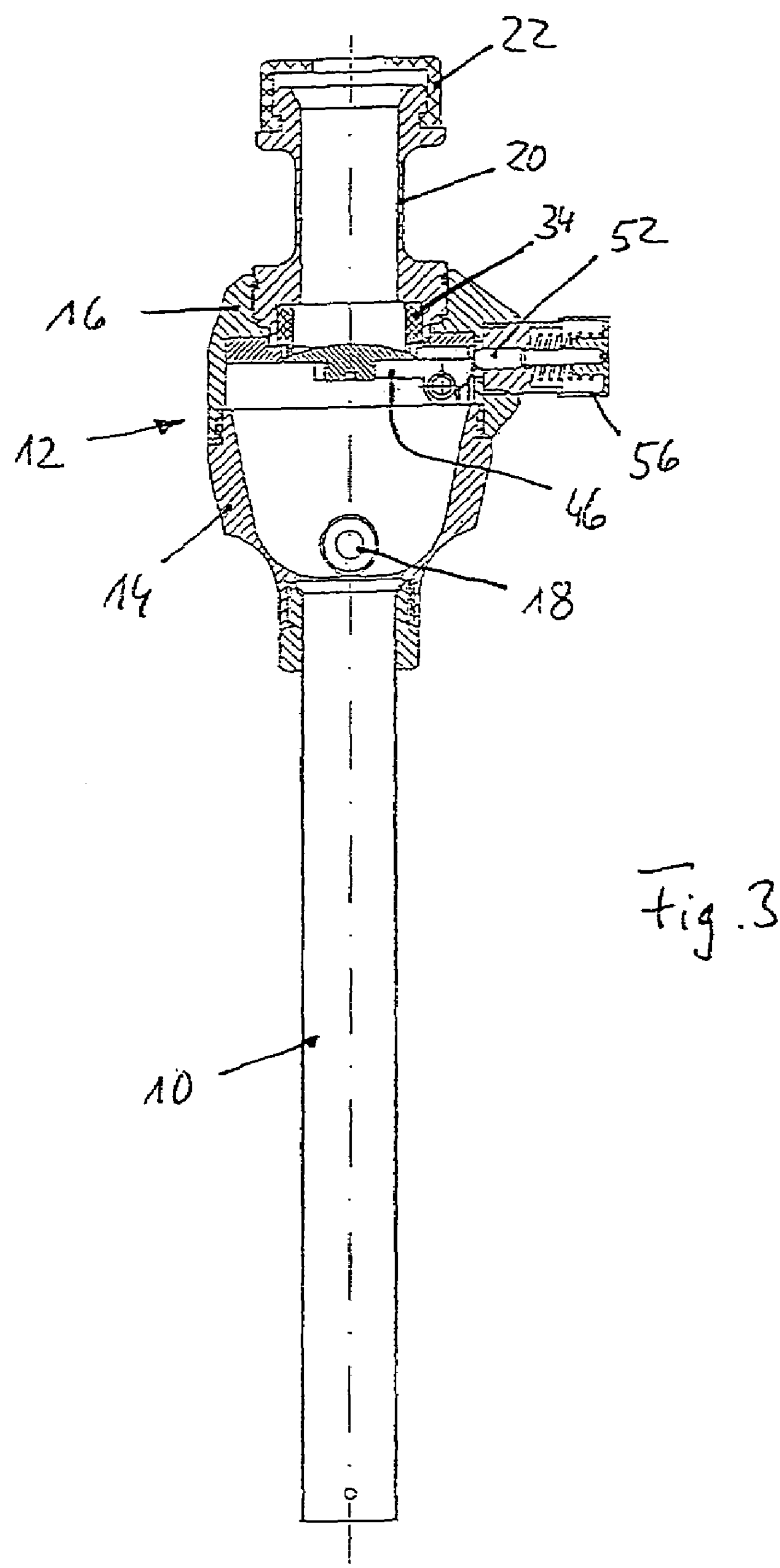
FIG. 3: an axial section of the trocar system.

The trocar system shown in FIGS. 1 through 3 includes a guide tube 10, containing an inserted trocar, not visible in the drawing, serving as instrument channel and access channel for minimally invasive surgery, for example, when inserted through the visceral cavity.

On the proximal end of the guide tube 10 a housing 12 is seated axially flush, comprising a base part 14 and a flap body 16. An insufflation stop-cock or valve 18 leads into the base part of the housing, through which gas can be injected into the visceral cavity. The flap body contains the flap valve, which is described in detail below. A hollow insertion shaft 20 is proximally screwed in sealed manner into the flap body 16, which is aligned axially with the insertion tube 10 and also exhibits the same inner diameter. On the proximal end of the insertion shaft 20, a soft elastic rubber covering 22 is attached, which exhibits a central opening and a diameter slightly smaller than the inner diameter of the insertion shaft 20.

Figure 4:
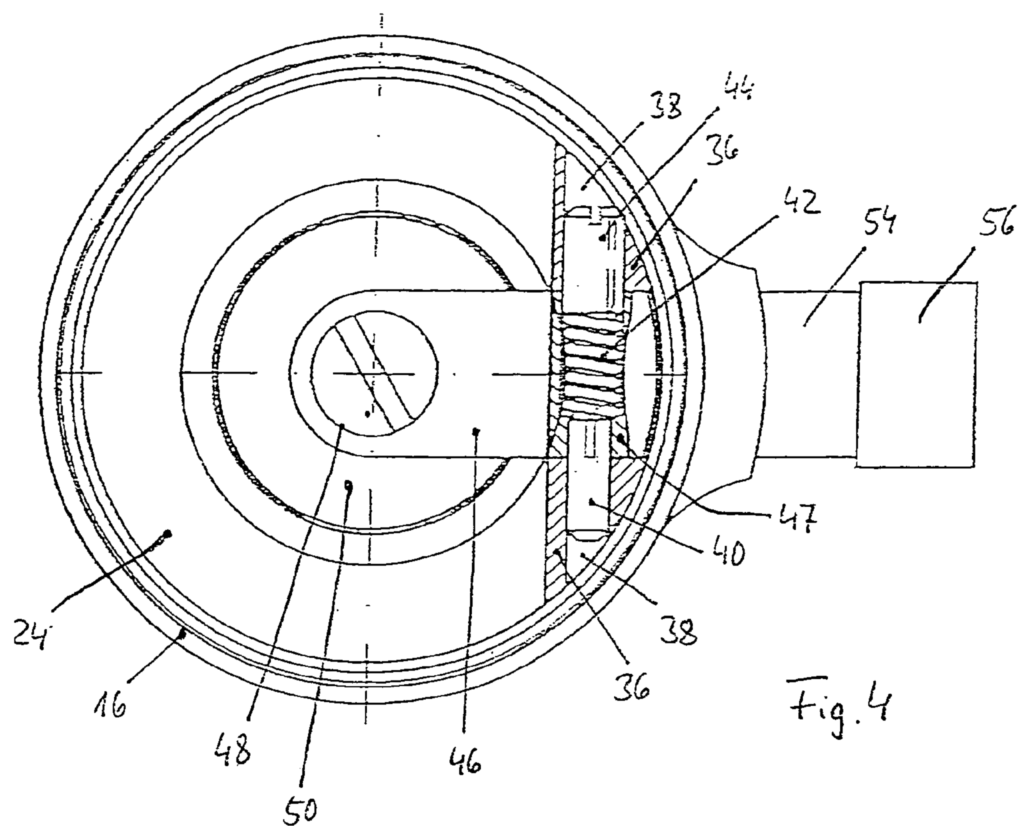
FIG. 4: an axial view of the flap valve from the distal side.
Figure 5:
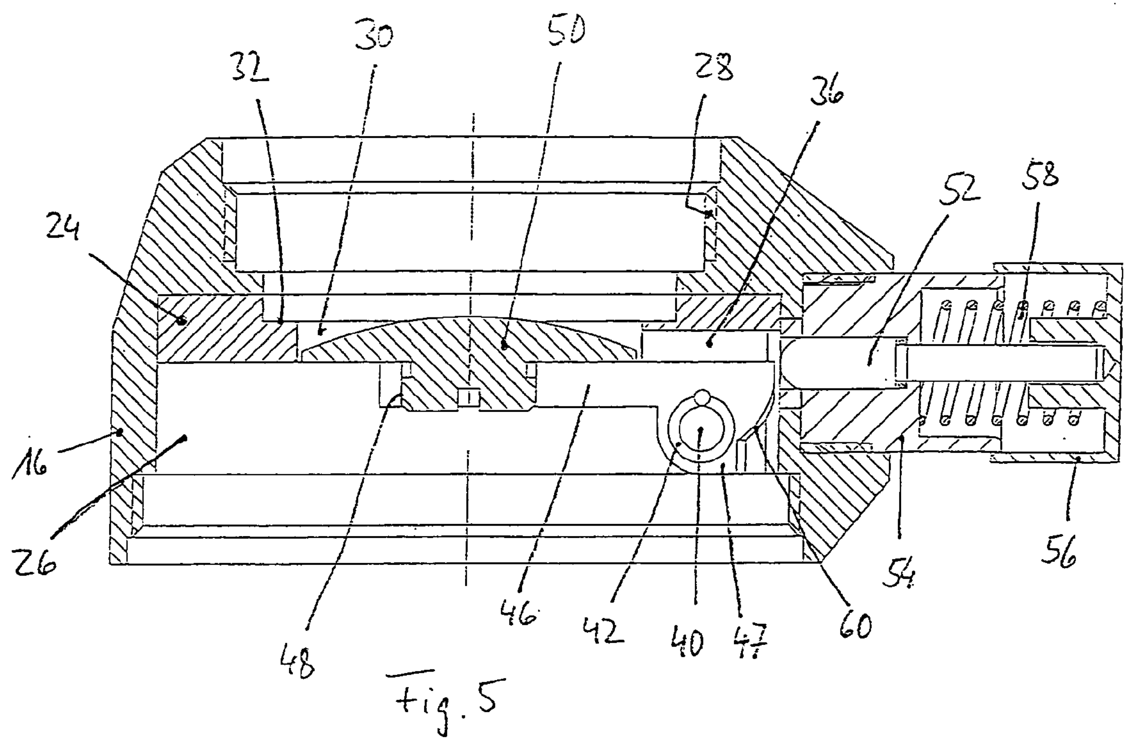
FIG. 5: an axial section through the flap valve in the "closed" position
Figure 6:
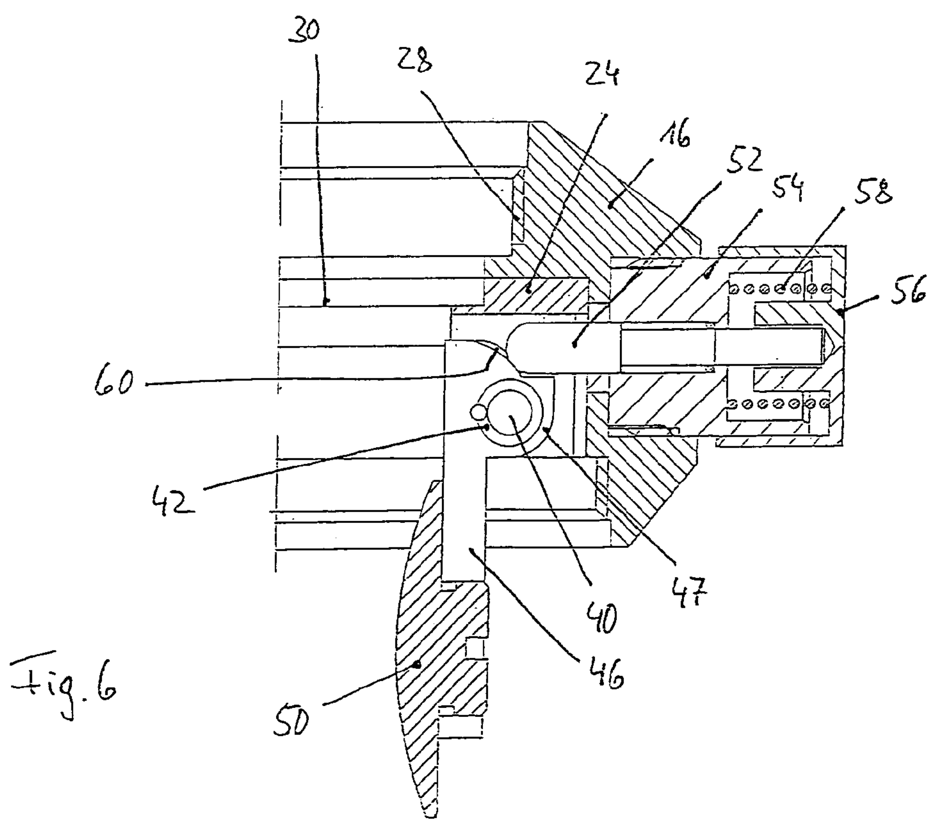
FIG. 6: an axial section through the flap valve in the "open" position

In FIGS. 4 through 6, the flap body 16 together with the therein arranged flap valve is shown in detail. The flap body 16 has a distal cylindrical chamber 26 that attaches at the base to the base part 14, into which a valve receptacle 24 is fitted. The chamber transitions co-axially into an opening, which exhibits an inner thread into which the insertion shaft 20 is screwed. The valve receptacle 24 has a lead-through opening 30 with its inner diameter smaller than the diameter of the opening of the body of the flap 16. Thereby, the valve receptacle 24 serves as an inner shoulder 32. An elastic gasket bushing 34 is fitted axially between the valve receptacle 24 and the insertion shaft 20. It is attached between the inner shoulder 32 of the valve receptacle 24 and inner shoulder of the insertion shaft 20, as shown in FIG. 3. The gasket bushing 34 extends co-axially into the lead-through opening 30 of the valve receptacle 24 and serves as the valve seat for the flap valve.

Two bearing supports 36 are positioned outside the outer diameter of the lead-through opening 30 on the flap retainer. Between the two bearing supports 36 there remains free a radial receptacle space. Both bearing supports 36 show respectively a flush-running bore 38 in the secant direction. A bearing pin 40 is inserted into the bore of one of the bearing supports. A leg spring 42 is co-axially attached upon the bearing pin 40. The leg spring 42 is held by a bearing bolt 44 which sits in the bore 38 of the other bearing support 36 and is co-axially screwed on to the bearing pin 40. The bearing pin 40 and the bearing bolt 44 pivotally hold flap 46. The flap 46 is housed between the bearing supports through a modeled block which is a lead-through-drilling flush to the bearing bore 38, and houses the bearing pin 40 with the leg spring. The leg spring 22 has one leg in the valve receptacle 24 and is attached with its other leg to the flap 46. The leg pin 42, therefore, provides the flap 46 with a pretension in the pivoting direction, in which the flap 46 gets pivoted against the valve receptacle 24.

Figure 7:
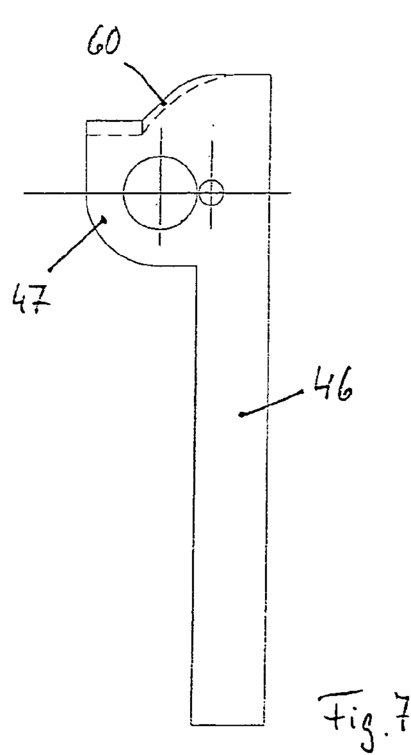
FIG. 7: an enlarged representation of the flap in side view
Figure 8:
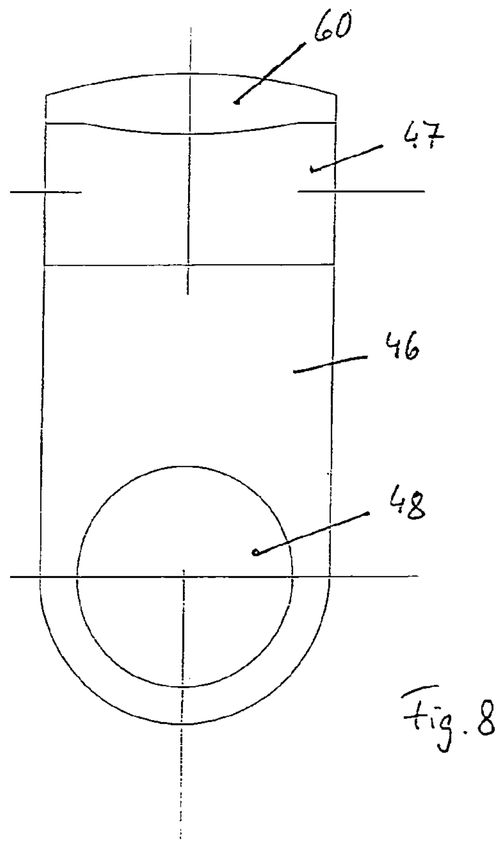
FIG. 8: a corresponding representation of the flap viewed from above

The flap 46, shown in FIGS. 7 and 8 as a single part, generally consists of a rectangular piece extending from the inner circumference of the chamber 26 radially towards inside and extends beyond the center axis of the flap body 16. At the radial outer edge of the flap 46, a mounting block 47 is formed on this distal area. Concentric to the middle axis of the body of the flap 16 and the lead-through opening 30, the flap 46 shows receptacle 48, into which a spherical calotte-shaped valve part 50 is screwed. The valve part 50 seals against the gasket bushing 34 when the flap 46, via the leg spring 42, is pivoted into the "closed" position, as shown in FIG. 5. Shown in FIG. 5 in the "closed" position, the flap 46 can be pivoted by a 90° turn into the "open" position against the force of the leg spring 42. In the "open" position, the flap 46 can be completely pivoted together with the valve part 50 in a distal direction, from the cross-section of the lead-through opening 30. In this "open" position, an instrument can be inserted through the insertion shaft 20, the lead-through opening 30 with the gasket bushing 34 and the guide tube 10 into the are where surgery is being performed. The instrument can be a surgical instrument, an endoscope or anything similar.

The pivoting of the valve 46 from the "closed" position into the "open" position is executed via slide rod 52. The slide rod 52 is guided radially through the flap body 16, and is displaceable in the radial direction along a plane perpendicular to the center axis of the flap body 16. The slide rod 52 is guided in a bushing 54, which is screwed into the body of the flap 16 radially and from the outside. The outer end of the bushing 54 is enclosed by a co-axial pushbutton 56. The pushbutton 56 is pressed upon the radial outer end of the slied rod 52. A helical compression spring is inserted co-axial to the slide rod axially between the bushing 54 and pushbutton 56 and tensions the pushbutton 56 and the therewith firmly connected slide rod 52 in the rest position shown in FIG. 5. The slide rod 52 is withdrawn radially from the chamber 26 of the body of the flap 16. Through manual pressure on to the push button 56, the slide rod 52 can be pushed into the body of the flap 16 radially against the force of the helical compression spring to operate the flap 56 and pivot from the "closed" position, as shown in FIG. 5, into the "open" position, as shown in FIG. 6.

In order to pivot the flap 46 using the slide rod 52, the flap 46 is constructed as follows. The pivot axis of the flap 46, formed by the bearing pin 40 and the bearing bolt 44, runs through a mounting block 47 and is distally offset from the plane of the flap 46. Therefore the area of the flap 46 runs eccentric in relation to the pivot axis. The axis of the slide rod 52, which corresponds with the direction of the linear movement, is constructed in a way that it nearly corresponds with the proximal topside of the flap 46, when the flap 46 is in the position shown in FIG. 5. An actuation area is defined on the flap 46 where the slide rod 52 is in contact with its inward directed end. The actuation area 60 is most easily seen in FIGS. 7 and 8. The actuation area 60 is located at the radial outer end of the valve part 50 away from the flap 46. The actuation area 60 starts at the proximal outer edge of the flap 46, runs in a distal direction until block 47 and gets increasingly closer to the predetermined pivot axis of the bearing pin 40. The radial distance of the actuation area 60 from the pivoting axis 40 therefore decreases from the proximal side of the flap 46 toward the mounting block 47. When starting the opening pivoting movement of the flap 46, the slide rod 52 pushes against the proximal side of the flap 46, parallel to the plane thereof, against the actuation area 60, which runs perpendicular to the plane of the flap area. At the end of the opening pivoting movement however, the slide rod 52 pushes perpendicularly to the plane of the flap area, against the section of the actuation area 60 which almost runs parallel to the plane of the flap area. Consequently, the linear movement of the slide rod 52 gets transformed into an angled pivoting movement of the flap 46, whereby the slide rod affects the actuation area almost perpendicularly throughout the complete pivoting movement and carries out the optimal pivoting momentum to the flap 46.

As shown in FIGS. 7 and 8, the actuation area 60, in the direction parallel to the pivoting axis, is slightly concavely arched, so it results in a good sliding area for the rounded inner end of the slide rod 52.

An ergonomically favorable handling of the trocar system is possible because a finger grip recess 62 is located at the distal end of the body 12, on both sides of the guide tube 10. The body 12 and, therefore, the whole trocar system is supported by positioning the index finger and the middle finger into these finger receptacles. The pushbutton 56 can be pushed with the thumb of the same hand to operate the flap valve.

10 Guide tube
12 Valve housing
14 Base part of the valve housing
16 Flap body
18 Insufflation valve
20 Insertion hollow shaft
22 Rubber covering
24 Valve receptacle
26 Chamber
28 Inner thread
30 Lead-through opening
32 Inner shoulder
34 Gasket bushing
36 Bearing support
38 Bearing bore

40 Bearing pin
42 Leg pin
44 Bearing bolt
46 Flap
48 Receptacle
50 Valve part
52 Slide rod
54 Bushing
56 Pushbutton
58 Helical compression spring
60 Actuation area
62 Finger grip recess

The invention claimed is:

1. A flap valve for a trocar system, with:

a valve housing, which is proximally attachable to a guide tube, an opening axially flush with the guide tube, a flap body including a flap that is pivotal about an axis perpendicular to and eccentric to an axis of the opening, and a slide rod, guided in the valve housing to be manually slidable and via which the flap can be pivoted out of a closed position in which the flap blocks said opening and into an open position in which said opening is unblocked, wherein the slide rod is slidable along a line which is substantially perpendicular to the axis of the opening and does not intersect a pivot axis of the flap, that the flap, relative to it's pivot axis, is a two-armed lever, of which one arm includes a valve part and one arm bears an actuation area, against which an inward end of the slide rod contacts, and that the actuation area is formed in a way, that in any pivot angle of the flap, a center axis of the slide rod forms, with a surface of the actuation area with which the slide rod is in contact, describes an angle of at least 15°.

2. A flap valve according to claim 1, wherein an angle of the center axis of the slide rod to the actuation area, in every pivoted angle of the flap is at least 30°, preferably at least 45°.

3. A flap valve according to claim 1, wherein the pivot axis of the flap is on its distal side and the actuation area is on the flap proximal from the pivot axis.

4. A flap valve according to claim 3, wherein the flap is disk shaped, that the pivot axis extends through a mounting block that is located on its radial outer edge on a distal side of the flap, and that the actuation area runs from a proximal outer edge of the flap to this mounting block.

5. A flap valve according to claim 4, wherein the center axis of the slide rod is positioned parallel and near a proximal area of the flap when the flap is resting in its "closed" position.

6. A flap valve according to claim 5, wherein the actuation area, at an area adjacent a proximal outer edge of the flap, against which the slide rod contacts when in a closed position of the flap, runs generally orthogonal to the proximal area of the flap, that a radial distance of the actuation area from the pivoting axis of the flap reduces going from the proximal outer edge of the flap towards the mounting block, and that the actuation area in its distal end area, against which the slide rod contacts when in an open position of the flap, has an angle of less than 45° to a plane of the flap.

7. A flap valve according to claim 1, wherein the slide rod is inserted into a bushing that is radially led into the valve housing and operates radially via a pushbutton against a force of a spring to open the flap.

8. A flap valve to claim 1, wherein recesses contoured to conform to fingers are provided distal to the valve housing, on both sides of the guide tube.

* * * * *